United States Patent [19]

Sweet et al.

[11] 4,367,043

[45] Jan. 4, 1983

[54] METHOD AND MEANS FOR DELIVERING LIQUID SAMPLES TO A SAMPLE SCANNING DEVICE

[75] Inventors: Richard G. Sweet, Palo Alto; Wayne A. Moore, San Francisco; Tom Nozaki, Jr.; Richard T. Stovel, both of Palo Alto, all of Calif.

[73] Assignee: Leland Stanford Junior University, Palo Alto, Calif.

[21] Appl. No.: 146,219

[22] Filed: May 5, 1980

[51] Int. Cl.³ .................... G01N 21/11; G01N 21/00; G01N 15/02
[52] U.S. Cl. .................................. 356/338; 340/712; 356/244; 356/440; 422/67; 435/219
[58] Field of Search ............... 356/244, 315, 417, 440, 356/442, 338; 250/222 PC; 340/286 M, 365 VL, 524, 525, 712; 435/219, 808; 422/67; 324/71 CP

[56] References Cited

U.S. PATENT DOCUMENTS

| | | | |
|---|---|---|---|
| 3,163,699 | 12/1964 | Staunton | 356/315 |
| 3,704,953 | 12/1972 | Carter et al. | 356/244 |
| 3,781,120 | 12/1973 | Engelhardt | 356/244 |
| 3,826,364 | 7/1974 | Bonner et al. | 209/638 |
| 3,976,429 | 8/1976 | Ginsberg | 324/71 CP |
| 4,222,036 | 9/1980 | Troukens | 340/286 M |
| 4,240,029 | 12/1980 | Haynes | 324/71 CP |
| 4,312,591 | 1/1982 | Tomoff | 356/315 |

*Primary Examiner*—Vincent P. McGraw
*Attorney, Agent, or Firm*—Donovan J. DeWitt

[57] ABSTRACT

Method and apparatus for semi-automatic feeding of liquid samples from a plurality of sample sources to a scanning device are disclosed. The liquid samples are picked up from a preidentified sample source and delivered to the scanning device by use of a hand-held pick-up and delivery tube. The hand-held tube is releasably coupled to the scanning device for delivery of the liquid samples to the scanning device when coupled thereto. In the disconnected condition, particle free fluid flows in a reverse direction from the scanning device for automatic flushing of the scanning device and liquid sample supply line connected thereto. Visual display means for visually indicating to the operator which sample holder the next sample is to be obtained from is provided.

38 Claims, 7 Drawing Figures

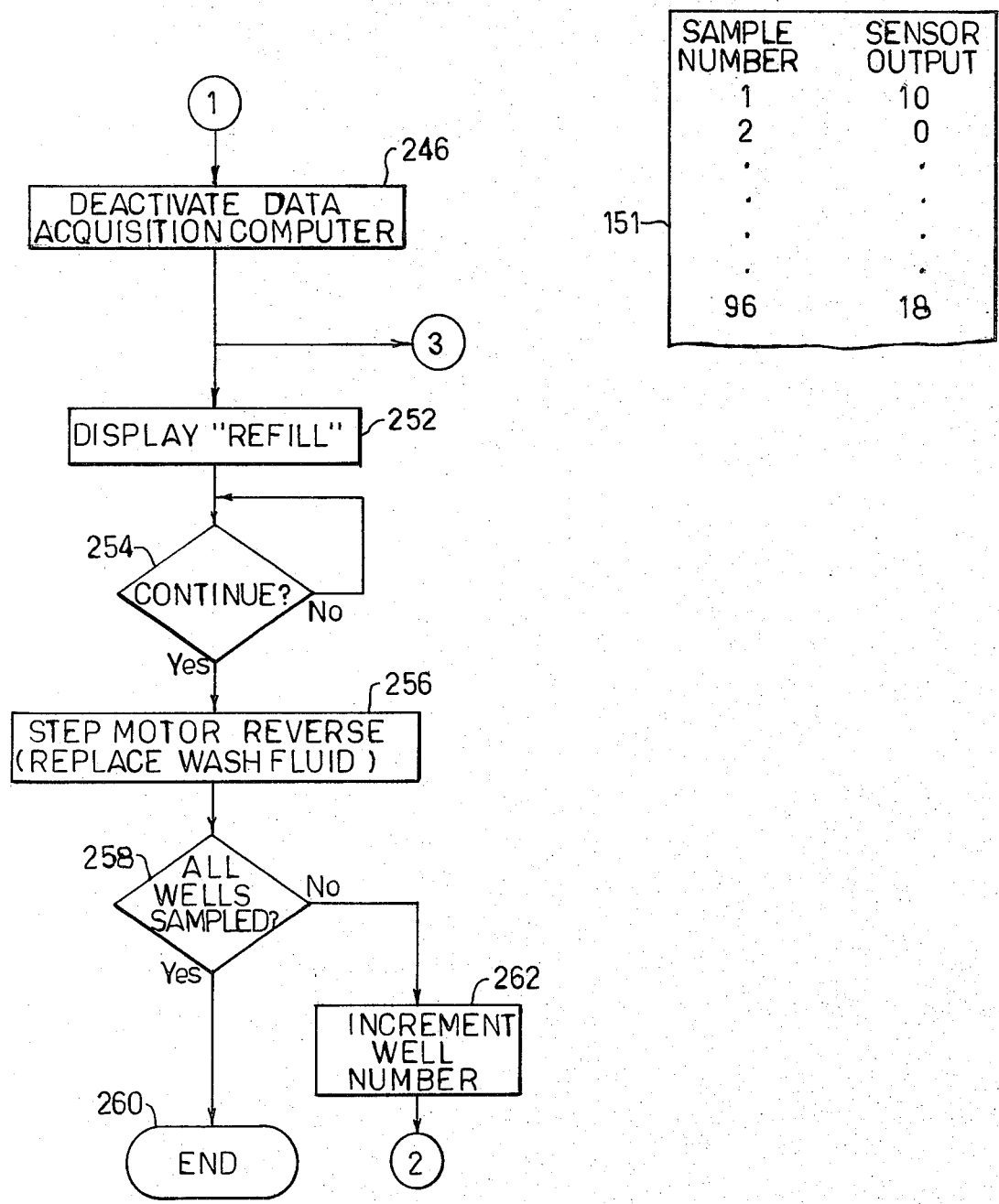

METHOD AND MEANS FOR DELIVERING LIQUID SAMPLES TO A SAMPLE SCANNING DEVICE

This invention was made with government support under Grant GM 17367 awarded by the Department of Health and Human Services. The Government has certain rights in this invention.

BACKGROUND OF THE INVENTION

Scanning devices for analyzing liquid samples delivered thereto are well known, which devices employ electrical, optical, acoustical, or like means, for making desired measurements on the samples. Some such devices are best adapted for operation on a single sample of relatively large volume. After feeding the sample through the device, operation is stopped and the sample delivery portion thereof is washed in preparation for another sample. This may require substantial time and often dismantling of the device. Other such scanning devices for handling large numbers of samples are fully automated, requiring substantially no operator attention or assistance. Such devices are complicated and expensive. The present invention is directed to an inexpensive, semi-automatic, sample delivery system for scanning devices whereby a relatively large number of small samples may be fed to the scanning device under operator control with minimum inconvenience over a short time period.

SUMMARY OF THE INVENTION AND OBJECTS

It is a general object of this invention to provide an improved liquid sample delivery method and apparatus for scanning devices which overcome the above-mentioned shortcomings and difficulties of prior art devices. A more particular object is to provide a small liquid sample delivery method and apparatus for scanning devices whereby a large number of samples are semiautomatically fed to the scanning device under operator control.

Another object of this invention is to provide a sample delivery method and apparatus of the foregoing type which includes visual instruction means for display to the next step in a sequence of steps to be performed by the operator.

A related object is to locate said visual instruction means for viewing of the instructions through a light-transmitting microtest tray, one of which instructions identifies the tray well from which the sample is to be removed.

Another object of this invention is the provision of a liquid sample delivery method and apparatus of the foregoing type for use with a scanning device utilizing a flow stream of particle-free liquid within which the liquid sample is injected, wherein said particle-free liquid is used for reverse flushing of at least a portion of the sample delivery system.

The above and other objects and advantages of this invention are achieved by use of a hand-held pick-up and delivery tube, or nozzle, attached to a reversible pump through a flexible line. The hand-held tube is manually releasably coupled through a sample supply line to a scanning device to which particle-free fluid also is supplied. In one particular type of prior art scanning device, the sample supply line leads to the inner nozzle of a pair of coaxially mounted nozzles included in a nozzle assembly. Particle-free sheath fluid is supplied to the outer nozzle to provide for a coaxial flow stream wherein the sample liquid is included in the inner stream portion and sheath fluid comprises the surrounding stream portion. The releasable coupling means for the hand-held nozzle includes an injection cone, comprising a funnel-shaped member into which the hand-held pick-up and delivery tube may be inserted in fluid-tight engagement therewith. With the hand-held tube removed from the cone, particle-free sheath fluid is driven backward through the sample supply line for washing the same between sample analysis.

Samples to be delivered to the scanning device are contained in the wells of a light-transmitting tray, such as a 96 well microtest or microculture tray formed with an 8×12 array of wells. A support is provided for the tray, and instruction, or message, means, such as a dot matrix display visible through the tray is provided thereat for display of the next step of a sequence of steps to be performed by the operator. A microcomputer is provided for control of the instruction means, which microcomputer, in turn, is stepped by use of a push button under operator control. Among other things, the microcomputer provides a sample source, or well, identification signal to the display for energization thereof in a manner identifying the well into which the pick-up and delivery tube is to be inserted by the operator for subsequent delivery of a sample therefrom to the scanning device for analysis thereof. The reversible pump also is controlled by outputs from the microcomputer for proper operation thereof. During passage of the sample through the scanning device, data is obtained thereon and supplied to data acquisition means, such as the memory of a data acquisition computer. The sample source identification signal from the microcomputer also is supplied to the data acquisition means for identifying the data output from the scanning device with the sample well.

BRIEF DESCRIPTION OF THE DRAWINGS

The nature of the present invention will be more fully apparent and understood from consideration of the following description in light of the drawings. In the drawings, wherein like reference characters refer to the same parts in the several views:

FIGS. 3A and 3B, together comprise a flow diagram showing a sequence of steps involved in delivering samples to the scanning device using the sample delivery system of this invention;

FIG. 4 is a fragmentary view of a print out of the type which may be obtained from the data acquisition means of the scanning device when used with the novel sample delivery system of this invention;

DETAILED DESCRIPTION OF THE INVENTION

Figure 1:
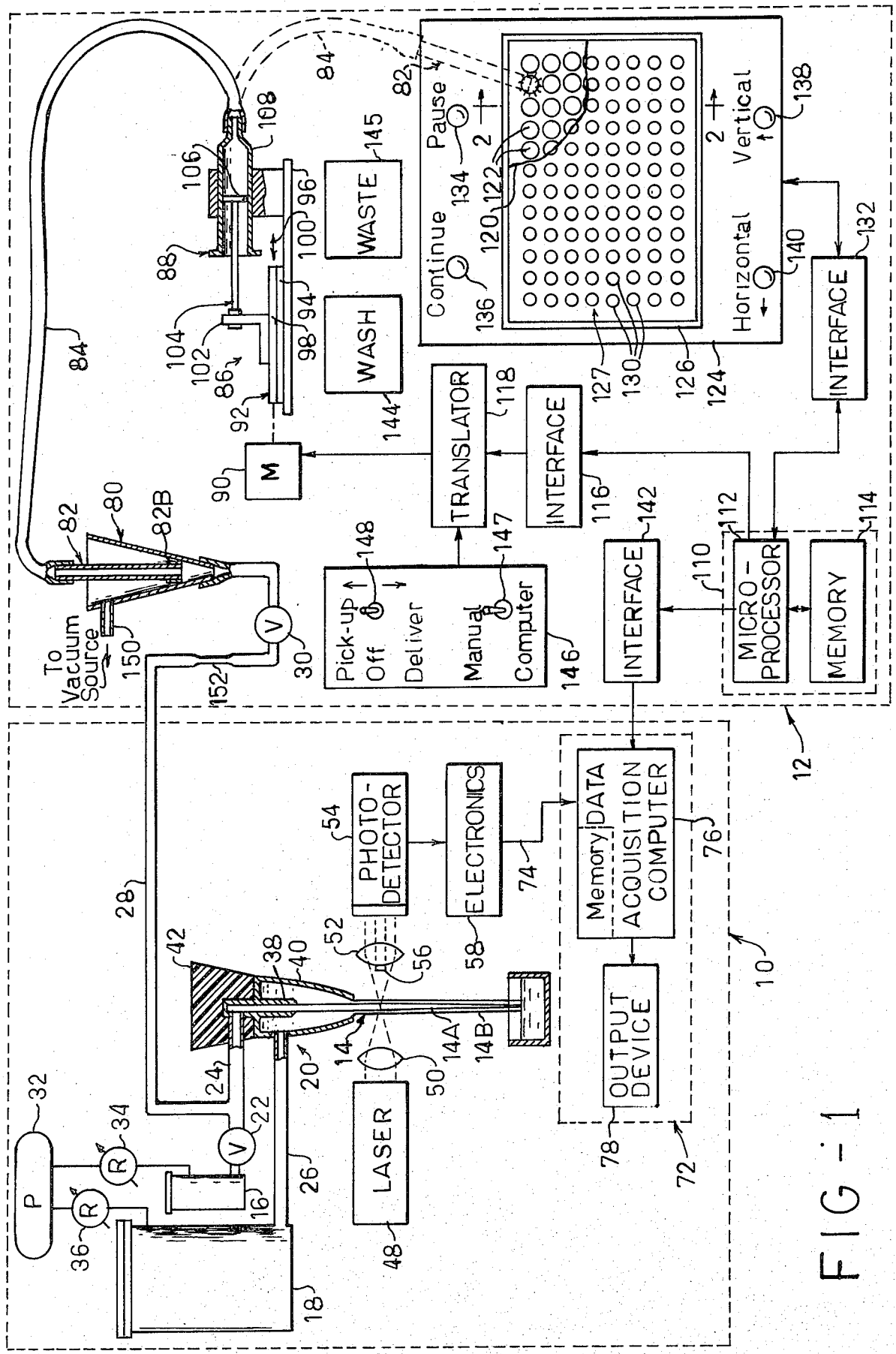
FIG. 1 is a diagrammatic showing of a sample scanning device and one embodiment of a novel sample delivery system of the present invention for use in feeding samples thereto.

Reference first is made to FIG. 1 wherein a substantially conventional sample scanning device 10 is shown, together with a multiple sample delivery system 12 for feeding samples thereto, which delivery system embodies the present invention. The illustrated prior art scanning device 10 is of the type which includes fluid flow means for producing a coaxial flow stream 14 comprising an inner sample-containing portion 14A and outer particle-free sheath portion 14B. The scanning device includes sample sensing means of any known type for obtaining signals related to at least one characteristic thereof. Electrical, optical, acoustical, or the like, sensing means may be used. For purposes of illustration only, and not by way of limitation, a scanning device 10 which includes optical sensing means is shown. A scanning device of the same type shown in U.S. Pat. No. 3,826,364, Bonner et al, which patent is assigned to the assignee of the present invention, may be used. The entire disclosure of this patent specifically is incorporated by reference herein.

The illustrated prior art particle scanning apparatus which is adapted for analyzing a large volume sample, includes pressurized reservoirs 16 and 18 containing a supply of the sample liquid in which particles to be analyzed are suspended, and particle-free sheath fluid, respectively. The reservoirs 16 and 18 are connected to a nozzle assembly 20; reservoir 16 being connected thereto through valve 22 and conduit 24, and reservoir 18 being connected thereto through conduit 26. It here will be noted that the novel multiple sample delivery system 12 is connected to the nozzle assembly via conduit 28 and valve 30. Valve 30 is closed and valve 22 is opened when sample liquid is to be supplied from the reservoir 16, in which case the multiple sample delivery system is disconnected from the scanning device. The reservoirs 16 and 18 are pressurized as by means of a gas pressure source 32 connected to the reservoirs through adjustable pressure regulators 34 and 36, respectively.

The illustrated nozzle assembly 20 includes interconnected first and second fluid passage means comprising inner and outer coaxially located nozzles 39 and 40 fixed to a mounting block 42 and supplied with fluid through the conduits 24 and 26, respectively. The structure is such that particle-containing sample fluid from the nozzle 38 is injected into the center of the flowing sheath fluid, with the coaxial flow stream 14 emerging from the nozzle assembly. Particle sensing means for making one or more measurements on the particles contained in the sample in the inner portion 14A of the coaxial stream 14 are provided. For purposes of illustration, optical sensing means are shown which include a laser 48 focused on the inner coaxial stream portion 14A by lens system 50. An objective lens 52 is provided in the beam path for focusing scatter beams onto the face of a detector 54. A mask 56 blocks out direct illumination from the laser 48 whereby only laser illumination scattered from illuminated particles in the stream reach the detector 54. The output from the detector 54 is supplied to electronic circuitry 58.

Data concerning particles sensed during the scanning of the samples is sent from electronic circuitry 58 to data acquisition means 72 over line or bus 72. Data of any type available from the detector 54 and associated electronics 58 may be supplied to the data acquisition means 72. For example, a count of the number of particles sensed may be made. The data acquisition means 72 simply may comprise a recorder for recording such information. In FIG. 1 the data acquisition means 72 is shown comprising a computer 76 and associated output device 78 such as a CRT terminal, printer, or the like.

As noted above, the above-described scanning device 10 is of conventional design and, if desired, may include particle sorting means, not shown, such as included in the above-mentioned U.S. Pat. No. 3,826,364. A relatively large volume of sample liquid may be contained in reservoir 16 for relatively long scanning operations. When other samples are to be analyzed, sorted, tested, or the like, a substantial amount of time often is required in preparing the device for operation, including time required for cleaning the sample reservoir 16, conduit 24, and nozzle assembly 20 for removal of all traces of the earlier-run sample. The multiple sample delivery system of the present invention, now to be described, allows for rapid scanning of a plurality of samples without the need for long delay periods for cleaning between samples, while at the same time providing for direct association of the sample source with data obtained from the sample to avoid confusion as to which sample produced the data acquired.

As seen in FIG. 1, the multiple sample delivery system 12 is connected to the scanning device 10 by closing valve 22 and opening valve 30 in line 28. The line 28 is attached to quick disconnecting coupling means 80 for use in removably connecting a hand-held pick-up and delivery tube, or nozzle, 82 to the scanning device. In FIG. 1 the coupling means 80 is shown comprising a funnel-shaped injection cone into which the hand-held tube 82 may be inserted in fluid-tight engagement therewith. Only a small force is required on the tube to provide for such sealing engagement, and the tube is readily removed from the injection cone with a minimum force.

Flexible tubing 84 connects the hand-held tube 82 to motor-operated pump means 86 for pumping fluid through the nozzle. Preferably, the pump is adapted for precision volume pumping of fluids and, for purposes of illustration, is shown comprising a syringe 88 driven by motor 90 through mechanical connection means 92, such as a micrometer mechanism, translation stage, or the like. Again for purposes of illustration, a translation stage is shown comprising a fixed member 94 attached to base plate 96, and longitudinally movable member 98 movable by motor 90 in the direction of double-headed arrow 100. A bracket 102 on the member 98 connects the translation stage to the plunger 104 of the syringe 88. The plunger includes a piston 106 slideably sealingly received in the cylinder 108 of the syringe. The flexible hose 84 is attached to the syringe cylinder 108 for movement of fluid contained therewithin in either direction depending upon the direction of movement of the piston 106.

A computer such as the microcomputer 110, comprising a microprocessor 112 and memory 114 is included in the system, which computer has an output connected to the motor 90 through an interface 116 and translator 118. In the illustrated arrangement the motor 90 comprises a stepper motor whose shaft is rotated a specified amount in either direction for each input pulse supplied thereto from the translator 118 for producing precise linear motion of the syringe pump. The rate at which pulses are supplied to the motor is controlled by the computer 110 for controlling the rate at which fluid is pumped.

Figure 2:
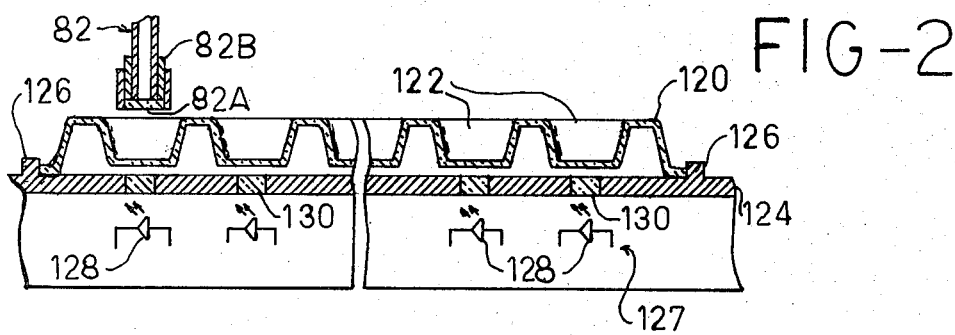
FIG. 2 is an enlarged fragmentary sectional view taken substantially along line 2—2 of FIG. 1 showing the tray support and associated instruction means visible to the operator through a tray.

In the illustrated arrangement multiple liquid samples to be supplied to the scanning device 10 are obtained from the wells of a tray 120, fragmentary plan and cross-sectional portions of which are shown in FIGS. 1 and 2, respectively. Microculture, or microtest, trays formed of light-transmitting material may be employed. For purposes of illustration, a 96 well tray is shown which is formed with an $8 \times 12$ array of wells 122. The tray is supported on a horizontal panel 124 formed with upright rails 126 inside of which the tray fits for tray-positioning purposes. An $8 \times 12$ array 127 of light sources, such as light-emitting diodes (LED) 128 (FIG. 2), matching the $8 \times 12$ array of tray wells is positioned beneath panel 124 for viewing through the panel and through the wells of the tray positioned thereon. In the illustrated arrangement an opaque panel formed with light-transmitting windows 130 through which the LEDs 128 are viewable is provided. Obviously, a glass, or transparent or translucent plastic panel section could be employed, together with opaque dividers between the LEDs to limit lighting to areas directly beneath the wells 122. The light source array comprises an LED dot matrix display for the display of operator instructions, including identification of the well from which the sample is to be removed. An interface 132 connects the LED array to the computer 112 for control of the display in a manner described in detail hereinbelow.

Momentary push-button switches 134, 136, 138 and 140, labelled PAUSE, CONTINUE, VERTICAL and HORIZONTAL, respectively, are provided at the front panel 124 which switches also connect to the computer 110 through the interface 132 for providing inputs to the computer. The PAUSE switch 134 enables the operator to stop delivery of a sample to the scanning device during a sample run. Delivery of the sample is resumed by actuation of the PAUSE switch 134. The sample delivery system automatically stops between certain steps of the delivery process, and the CONTINUE switch 136 is used to initiate operation of the next step when the operator is prepared therefor. The respective vertical and horizontal switches 138 and 140 are used for controlling a sample source, or well, identification signal which, among other things, controls the LED to be illuminated for identifying the tray well from which the sample is to be removed. The same sample source identification signal also is supplied to the data acquisition means 72 through an interface 142 for associating the data obtained from the scanning device with the sample source from which the sample was supplied which produced the data. These functions are described in greater detail hereinbelow with reference to the flow diagram of FIGS. 3A and 3B.

The multiple sample delivery system is prepared for semiautomatic operation by first filling the pick-up and delivery tube, or nozzle, 82 and flexible tubing 84, and partially filling the barrel 108 of the syringe pump 88 with wash liquid, such as a saline solution, obtained, for example, from a container 144 thereof. To facilitate this operation, the stepping motor 90 is provided with a manually operated control circuit 146 which includes a two-position "Manual/Computer" switch 147 and a three position switch 148 movable between "Off", "Pick-up" and "Deliver" positions. In the "Manual" and "Pick-up" positions of the respective switches 147 and 148, the motor is stepped in a reverse direction to move the syringe piston outwardly of the cylinder, and in the "Deliver" position of switch 148, the motor is stepped in a forward direction to move the piston inwardly within the cylinder. The pick-up tube 82 is inserted in the wash container 144 and the switch 148 actuated to the pick-up position to partially fill the syringe pump with wash liquid. The motor 90 is placed under control of the microcomputer 110 when switch 147 is in the "Computer" position.

As noted above, valve 22 from the large sample reservoir 16 is closed and valve 30 in conduit 28 leading to the injection cone 80 is opened when use of the multiple small sample delivery system is to be made. Sheath fluid 14B from reservoir 18 is supplied, under pressure, to the nozzle assembly 20 of the scanning device 10 through conduit 26. With the hand-held pick-up and delivery tube 82 removed from the injection cone 80, sheath fluid is driven in a reverse direction through inner nozzle 38, connecting conduits 24 and 28 and valve 30, to the injection cone 80. The injection cone fills with sheath fluid to the leval of a vacuum line 150 extending from the side of the cone and connected to a vacuum source, not shown. When filled to the vacuum line, sheath fluid is drawn off by the vacuum source and, in this manner, a constant backwashing of the connecting tubing and nozzle 38 is provided for washing purposes and for the removal of previously injected air bubbles therefrom. Preferably, a flow restrictor 152 is included in the line 28 to the injection cone to limit the flow rate of fluid passing therethrough, thereby conserving the amount of sheath fluid expended during the continuous backwashing mode which occurs when the sample pick-up and delivery tube 82 is uncoupled from the conduit 28, i.e. whenever the tube 82 is removed from the injection cone.

OPERATION OF MULTIPLE SAMPLE DELIVERY SYSTEM

Figure 3A:
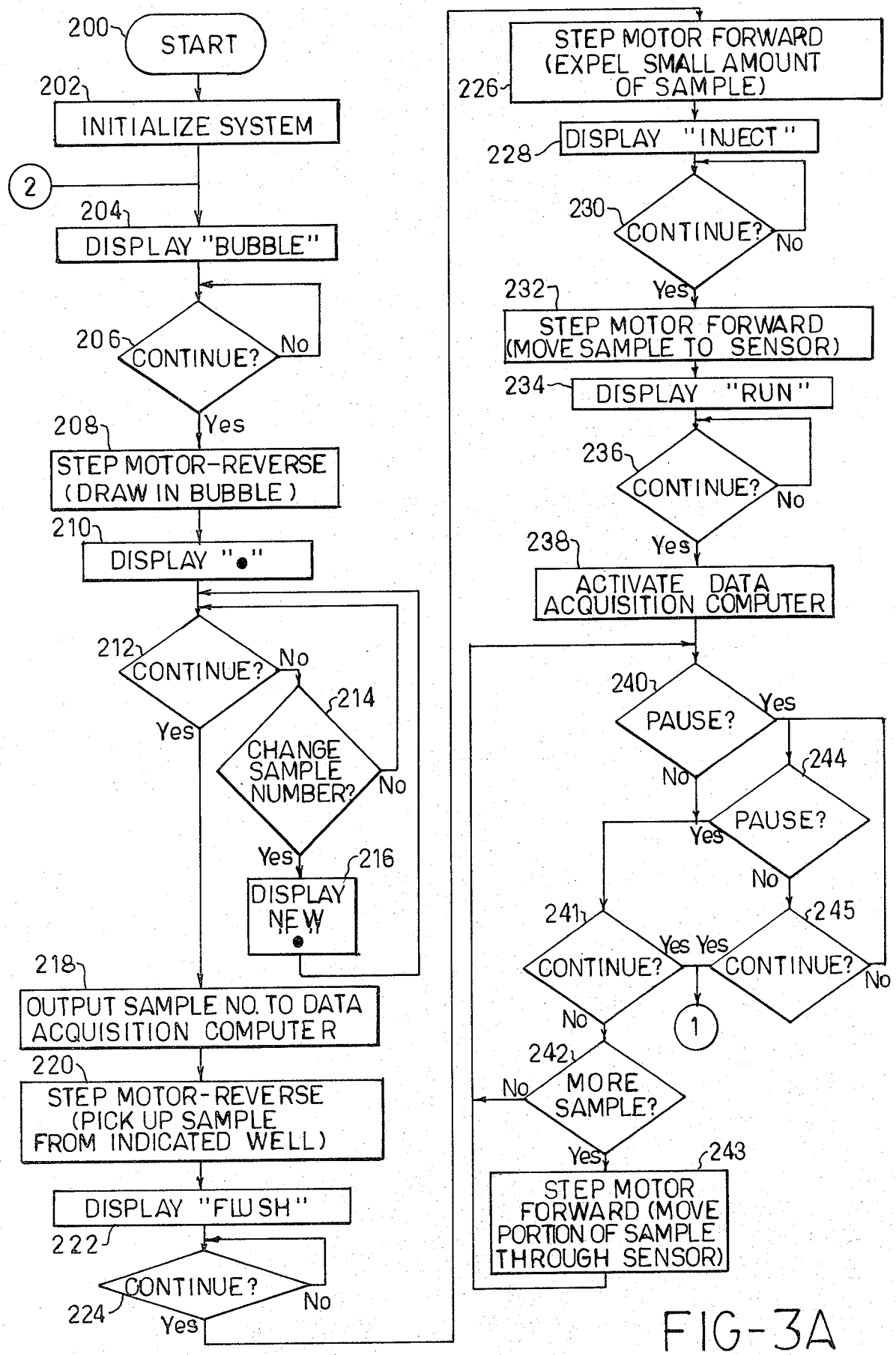

FIGS. 3A and 3B, together, show a flow chart of an algorithm for stored program operation of the multiple sample delivery system shown in FIG. 1. Various operations indicated therein are under control of the microprocessor 112 responsive to programming instructions contained in memory unit 114. Obviously, one or more programming steps may be involved in the actual implementation of the indicated operations. Since the programming of such steps is well within the skill of the average programmer, a complete program listing is not included herein.

Following a START step 200, when power for the sample delivery system is first turned on, or a reset operation is performed, by means not shown, the system including computer 110 is initialized. Initialization step 202, includes setting a "sample nunber" counter in memory 114 to "1". Following initialization, the word "BUBBLE" is displayed (step 204) at the LED array 127 which is viewable through the sample-filled tray 120 positioned over the display. (If not done previously, the pump 86 is primed using the switches 147 and 148 at control circuit 146, in the manner described above, to load the sample pick-up and delivery tube 82 and attached tubing with wash solution.) The "BUBBLE" instruction indicates to the operator that an air bubble is to be drawn into the end of tube 82. The microprocessor next performs a decision step 206 to determine whether or not the CONTINUE switch 136 has been actuated. If not, the step 206 is again initiated, and a wait loop is entered. With display of the "BUBBLE" instruction, the tube 82 simply is held in the air, and the CONTINUE switch 136 is actuated by the operator whereupon the decision for step 206 is affirmative and step 208 is entered. Now, the stepping motor 90 is actuated in a reverse direction to draw a small volume of air, say, several microliters, into the tube 82. Step 210 then is entered for energization of one LED in the array 127 identifying the tray well from which sample liquid is to be withdrawn. This information is obtained from the above-mentioned "sample counter" which is initialized at the beginning of the first run. In FIG. 1, illumination of one tray well is shown, together with a broken line showing of the pick-up tube 82 at the so-identified well.

The decision step 212 then is entered to again determine whether or not the CONTINUE switch 136 has been actuated. If not, decision step 214 is entered to determine whether or not either one or both of the VERTICAL or HORIZONTAL switches 138 and 140 have been actuated for changing the count in the "sample number" counter. If not, the decision step 212 is again initiated. If the sample number has been changed by actuation of switch 138 and/or switch 140, the new well-identifying LED 128 is energized at step 216. It will be apparent that samples from operator-selected wells may be analyzed, without the need to step through operations for each of the 96 tray wells. When the desired well is illuminated, the pick-up tube 82 is inserted in the indicated well, and the CONTINUE switch 136 is actuated. When the CONTINUE switch 136 is actuated, with the tube inserted in the LED-identified well, step 218 is performed. Before describing step 218, it first will be noted that filtering of the sample liquid often is required to prevent undesired large particles from being delivered to the scanning device 10 which could interfere with its operation. When filtering is required, a filter 82A (FIG. 2) may be attached to the end of the sample pick-up tube 82 before inserting the tube into the designated sample well. The filter is removed from the tube, and flushed, after removal of the liquid sample from the tray.

At above-mentioned step 218 the sample number contained in the contents of the "sample number" counter included in the microcomputer memory 114 is outputted to the data acquisition means 72. In the illustrated arrangement, wherein the data acquisition means comprises a computer 76, the sample number may be stored in the computer 76 memory, or the sample number may be used to control the storage location at which data obtained from the subsequent scanning operation is stored. In any event, an association is provided between the sample number and the scanning data to identify the sample source with the data. Step 220 is entered at which time a predetermined volume of liquid sample is picked up by the pick-up tube 82 from the indicated tray well.

Following step 220, the word "FLUSH" is displayed at the LED dot matrix display provided by array 127 (step 222) and the process proceeds to decision step 224 where a wait loop is entered pending actuation of the CONTINUE switch 136. The displayed word "FLUSH" instructs the operator that a small amount of sample is to be expelled from the pick-up and delivery tube 82 when the CONTINUE switch 136 is again actuated. The tube 82 is removed from the well, and the filter 82A is removed from the tube in preparation of such flushing step. Upon actuation of the CONTINUE switch 136, step 226 is entered for forward stepper motor operation to expel a small amount, say, less than one (1) microliter, of sample from the pick-up and delivery tube 82. This ensures that there will be no air bubbles at the end of the tube that might interfere with subsequent sample flow through the scanning device 10. A waste receptacle 145 (FIG. 1) is provided into which the sample may be flushed. Following this, the instruction "INJECT" is displayed at the array 127, as indicated at step 228, and decision step 230 is entered.

In response to the "INJECT" instruction, the operator inserts the tube 82 into the injection cone 80 as shown in the full line position of FIG. 1. The tube 82 is formed of rigid material, such as stainless steel tubing, to facilitate handling thereof. A short length of plastic tubing 82B, such as polyethylene tubing, is located over the tip end of the tube to provide for improved sealing engagement between the tube and injection cone. The cone may be of the type often used as a disposable plastic pipette tip. Because of the narrow taper angle of the cone, many types of tubing will seal adequately when inserted in the cone with small manual force. However, Teflon tubing does not seal well. The cone 80 is mounted vertically, as illustrated, on a mounting fixture, not shown.

With the pick-up and delivery tube 82 inserted in the cone 80 in sealing engagement therewith, the CONTINUE switch 136 is depressed, decision step 230 is affirmative, and step 232 is entered for forward drive actuation of the stepper motor 90. The motor is energized for rapid stepping thereof to rapidly drive the sample through the conduits 28 and 24 leading to the nozzle assembly 20 of the scanning device 10. Motor operation is stopped when the leading edge of the liquid sample reaches the nozzle assembly 20. After step 232, the instruction "RUN" is displayed (step 234) and operation proceeds to decision step 236.

The "RUN" instruction simply informs the operator that the sample is ready for passage through the scanning device 10. For proper operation, most scanning devices operate at a given flow rate, or range of rates. When the CONTINUE switch 136 is actuated, the data acquisition means 72 is activated (step 238) to condition the same for receiving and/or storing data produced during the subsequent sample scanning process. The decision step 240 then is entered for determining whether or not the PAUSE switch 134 has been actuated. If the PAUSE switch has not been actuated, the decision step 241 is entered for determining whether or not the CONTINUE switch 136 has been actuated and, if the decision is negative, another decision step 242 is entered for determining whether or not more sample liquid remains for analysis by the scanning device 10. If there is more liquid sample to be analyzed, or scanned, the stepper motor 90 is energized to drive a portion of the liquid sample past the sensor, or detector, 54 of the scanner (step 243). After step 243, the decision step 240 is again entered and, if the PAUSE and CONTINUE switches remain unactuated, operation within the loop continues until all of the liquid sample has been delivered to the scanning device 10 for analysis. When no more of the liquid sample remains for analysis, i.e. when the result of decision step 242 is negative, step 243 is by-passed thereby preventing further operation of the stepper motor 90 and delivery of liquid to the scanner. As will become apparent, actuation of the CONTINUE switch 136 now is required for the operation to continue.

Delivery of liquid sample during the sample run may be halted when desired by operation of the PAUSE switch 134. Decision step 240 provides means for entering a subroutine whereby the delivery of a liquid sample may be stopped and restarted. At decision step 240, if decision is affirmative, by actuation of the PAUSE switch 134, decision step 244 is entered. At step 244, operation of the PAUSE switch 134 is again checked and, if the switch is not actuated, the decision is negative and decision step 245 is entered. At decision step 245, if the CONTINUE switch 136 is not actuated, the decision is negative and operation loops back to the decision step 244. It will be seen then, that when the PAUSE switch is actuated once, delivery of the liquid sample to the scanning device is halted and remains halted so long as neither the PAUSE nor CONTINUE switch is actuated. Sample delivery is resumed simply by actuation of the PAUSE switch 134 a second time. Now, decision step 244 is affirmative, and operation proceeds to decision step 241, described above.

The sample run may be aborted at any time during the scanning operation simply by actuation of the CONTINUE switch 136. If, during delivery of a liquid sample, or immediately prior to delivery, following activation of the data acquisition computer 76 (step 238) CONTINUE switch 136 is actuated, decision step 241 is affirmative, and the data acquisition computer is deactivated (Step 246, FIG. 3B). It here will be noted that step 246 also may be entered from decision step 245 when delivery of the liquid sample is halted by operation of the PAUSE switch 134. Prevention, or termination, of a sample run as described above saves operator time when no information, or no additional information, concerning the sample is required before normal termination of the run.

Following deactivation of the data acquisition computer (step 246) the instruction "REFILL" is displayed at the LED dot matrix array 127 (step 252), and the decision step 254 is entered. For REFILL operation, the pick-up tube 82 is inserted into the wash receptacle 144 (FIG. 1) containing a saline solution, or the like. Now, when the CONTINUE switch 136 is actuated the stepper motor 90 is driven in a reverse direction (step 256) whereupon saline solution is drawn into the tube 82 and associated tubing to replace that which was expended while driving the sample through the tube. After such replacement of fluid, the tube 82 is removed from the receptacle and the filter 82A, if needed, is replaced on the tube tip in preparation for another sequence of operations for delivery of another sample to the scanning device. Decision step 258 is entered at which time the contents of the "sample counter" established in memory 114 of the microcomputer 110 is tested to determine whether or not it has reached the last sample number. If the decision is affirmative, the operation stops at step 260. If not, the "sample counter" is incremented (step 262) and operation returns to step 204 for display of the instruction "BUBBLE" for the start of another delivery cycle.

FIG. 4 to which reference now is made, shows an output 151 of the type which may be obtained from the output device 78, of data acquisition means 72. For purposes of illustration only columns labelled SAMPLE NUMBER and SENSOR OUTPUT are provided at output 151. In the illustrated arrangement, wherein samples are obtained from a microculture tray, the sample numbers identify tray wells. Obviously, samples may be obtained from containers other than multi-well trays, if desired. If, for example, the samples are obtained from individual containers, such containers may be labelled with the sample number, or, sequentially positioned whereby the sample number may be identified with a particular container. In FIG. 4, sample numbers 1, 2 and 96 are shown with associated sensor outputs of 10, 0, 18, respectively, which identify, for example, the number of particles having particular characteristics sensed in each of the samples.

Figure 5:
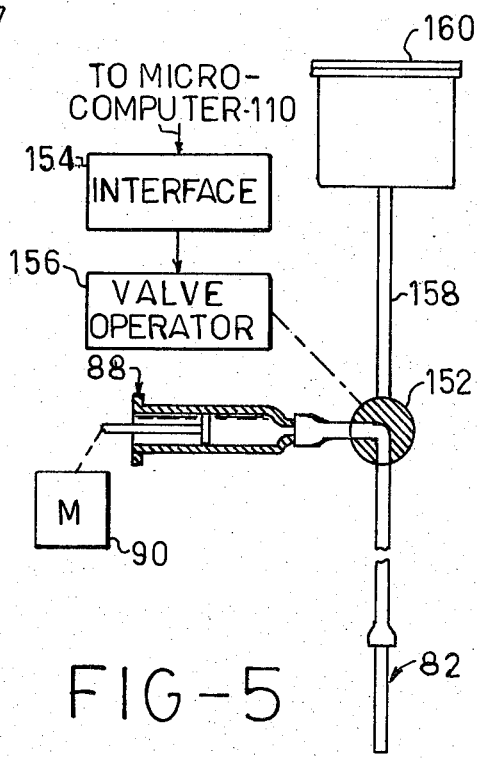
FIG. 5 is a fragmentary diagrammatic showing of a modified form of sample delivery system which also embodies the present invention.

The invention having been described in detail in accordance with requirements of the Patent Statutes, various other changes and modifications will suggest themselves to those skilled in this art. For example, one or more of the steps requiring operator attention may be more fully automated. In FIG. 5, to which reference is made, a fragmentary portion of a modified form of multiple sample delivery system is shown wherein saline solution which is expended during sample delivery is automatically replaced following a sample run without need for the operator to insert the pick-up and delivery tube 82 in a container thereof. In the FIG. 5 arrangement, the syringe pump 88 is connected to the hand-held tube 82 through a two-way valve 152 which is controlled by the microcomputer 110 through an interface 154 and valve operator 156. A third line 158 from the valve 152 leads to a reservoir 160 of wash liquid, such as a saline solution. The reservoir may be pressurized, if desired. After a liquid sample has been delivered to the scanning device, the valve 152 is rotated, under control of microcomputer 110, for connection of the syringe pump to the reservoir. Now, when the syringe piston is withdrawn from the cylinder, fluid is withdrawn from the reservoir 160 into the syringe. The valve 152 is rotated back to the position illustrated in FIG. 5 at which time the delivery system is in condition for the start of another delivery cycle.

Figure 6:
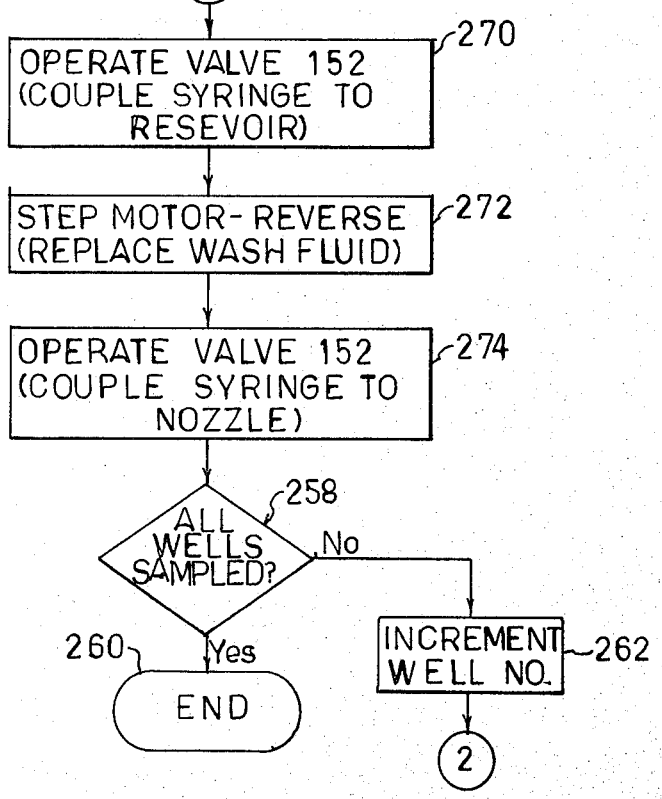
FIG. 6 is a portion of a flow diagram showing steps involved in operation of the FIG. 5 embodiment of the invention.

A suitable algorithm for use with the automatic refill system illustrated in FIG. 5 is shown in FIG. 6, to which Fig. reference now is made. The algorithm shown in FIG. 6 replaces that portion of the FIG. 3B algorithm between points 3 and 2 identified therein. Following a sample run, when the liquid sample has been discharged from the tube 82, the valve 152 is operated for connection of the syringe pump 88 to the reservoir 160 at step 270. The stepper motor 90 is operated in reverse (step 272) to draw saline liquid from the reservoir 160 into the syringe pump 88 to replace the volume thereof expended in the preceeding delivery of a liquid sample. When the motor stops, the valve 152 is returned to the position illustrated in FIG. 5 for connection of the syringe pump 88 to the nozzle 82 (step 274). The remainder of the steps 258, 260 and 262 are the same as shown in FIG. 3B and described above.

Also, it will be apparent that different pump means may be employed in place of the illustrated syringe pump 88. Peristaltic pump means may be used, for example, which is connected to a source of saline solution from the rear of the pump, thereby eliminating the need for the FIG. 5 arrangement to provide the system with replacement saline solution.

Often, the output from scanning devices include a histogram representing the distribution of particles sensed. Obviously, the sample number obtained from the sample delivery system of this invention may be associated with such histograms of the samples, or other processed output from the scanning device.

Liquid samples may, of course, be obtained from containers other than the illustrated microculture tray. They could be located in numbered containers, for example, in which case the sample identification signal could be supplied to a numeric display for visual display of sample source number (instead of, or in addition to, display of a single LED in the array 127) thus identifying the container from which the liquid sample is to be obtained. Obviously, the array 127 may be used for display of the container number in place of the "." instruction, in such a case. An input for selecting between such displays may be provided. However, by using microculture trays, in which cells to be scanned are grown, as the source of liquid samples, the need to transfer the samples to other containers is avoided. Fewer particles and less reagent may be required in the preparation of samples in microculture trays compared, for example, to the use of test tubes or other large containers. Also it will be apparent that the present system may include the use of another visual display means in addition to the array 127 for display of various operator instructions.

It is intended that the above and other such changes and modifications shall fall within the spirit and scope of the invention as defined in the appended claims.

We claim:

1. A multiple sample delivery system for use in sequentially feeding liquid samples from a plurality of sample sources to sample scanning, analyzing, and like means of the type which produces signals related to contents of the liquid samples, said system comprising
    sample source identification signal means for identifying individual sample sources from which liquid samples for delivery to sample scanning means are obtained,
    visual display means responsive to said sample source identification signal means for visually indicating to the operator the sample source from which the next liquid sample for delivery to the sample scanning means is to be obtained,
    means under operator control for obtaining liquid samples from the visually-indicated sample source, and
    means for feeding the liquid sample obtained from said visually identified sample source to said scanning means for producing signals related to contents or the liquid sample.

2. A multiple sample delivery system for use in sequentially feeding liquid samples from a plurality of sample sources to sample scanning, analyzing, and like means of the type which includes interconnected first and second fluid passages through which said liquid sample and particle-free liquid, respectively, are delivered for scanning of the sample, said system including
    means for feeding liquid samples obtained from different sample sources to said scanning means, and
    means for removably connecting said liquid sample feeding means to said first fluid passage means whereby, upon disconnection of said liquid sample feeding means from said first fluid passage means, said particle-free liquid delivered to said second fluid passage means of said sample scanning means flows in a reverse direction through the first fluid passage means for flushing said first fluid passage means when said sample feeding means is disconnected from said first fluid passage means.

3. A multiple sample delivery system as defined in claim 2 wherein said first and second fluid passage means of the sample scanning means comprise coaxial nozzles for producing a coaxial flow stream having an outer stream portion of particle-free liquid and an inner stream portion comprising said liquid sample.

4. A multiple sample delivery system as defined in claim 2 wherein said liquid sample feeding means includes a pick-up and delivery tube, pumping means connected to said pick-up and delivery tube for delivery under pressure of liquid samples from the tube, and wherein said means for removably connecting said liquid sample feeding means to said first fluid passage means includes an injection cone connected to the first fluid passage means into which cone said pick-up and delivery tube is removably received in fluid-tight engagement therewith during delivery of liquid samples to the scanning means.

5. A multiple sample delivery system as defined in claim 4 including suction means attached to a wall of said injection cone for removal of reverse-flushed particle-free fluid therefrom.

6. A multiple sample delivery system as defined in claim 4 wherein said pumping means comprises a motor-operated syringe.

7. A multiple sample delivery system for use in sequentially feeding liquid samples from a plurality of sample sources to sample scanning, analyzing, and like means of the type which produces signals related to contents of the liquid samples, liquid samples for delivery to said scanning means being obtained from a multi-well tray formed of light-transmitting material, said system comprising
    sample source identification signal means for identifying individual sample sources from which liquid samples for delivery to sample scanning means are obtained,
    means for feeding liquid samples from said identified sample sources to said scanning means for producing signals related to contents of the liquid samples,
    means for associating signals produced by said scanning means with said sample source identification signal means for identifying signals from said scanning means with the liquid sample source,
    supporting means for a multi-well, light-transmitting, tray from which liquid samples are to be delivered to said scanning means,
    dot matrix display means comprising an array of individual light source means at said supporting means arranged in a pattern corresponding to tray wells, and
    means for energizing said light source means for visual display of operator instructions viewable through a tray resting on said supporting means.

8. A multiple sample delivery system as defined in claim 7 wherein said means for energizing said light source means includes said sample source identification signal means for energizing individual light sources for identifying a single tray well from which a liquid sample is to be picked-up for subsequent delivery to the scanning means.

9. A multiple sample delivery system for use in sequentially feeding liquid samples from a plurality of sample sources to sample scanning, analyzing and like means of the type which produces signals related to contents of the liquid samples, said system comprising
    sample source identification signal means for identifying individual sample sources from which liquid samples for delivery to sample scanning means are to be obtained,
    means for feeding liquid samples from said identified sample sources to said scanning means for producing signals related to contents of the liquid samples
    a stored program digital computer for producing said sample source identification signal means and for control of said liquid sample feeding means, the delivery of liquid samples being carried out in accordance with a predetermined program requiring a sequence of steps, at least some of which require instruction to the operator, means responsive to the stored program for stopping operation of the feeding means between selected steps of the sequence, visual display means under control of the digital computer for display of the next step in the sequence of steps to be performed, and means under operator control for resuming operation of the feeding means.

10. In a multiple sample delivery system as defined in claim 9 including means under control of said sample source identification signal means for visually indicating to the operator the sample source from which the liquid sample for delivery to the sample scanning means is to be obtained.

11. In a multiple sample delivery system as defined in claim 10 wherein said means for visually indicating to the operator the sample source from which the liquid sample is to be obtained includes said visual display means for display of the next step in the sequence of steps to be performed.

12. In a liquid sample scanning, analyzing, separating, or like apparatus of the type which includes a fluid flow assembly commprising interconnected first and second fluid passages for use in producing a flow stream comprising sample liquid supplied to said first fluid passage and particle-free liquid supplied to the second fluid passage, an improved liquid sample delivery system for feeding liquid samples from a plurality of difference sample sources to the first fluid passage of the fluid flow assembly comprising, liquid sample pumping means, and means for removably connecting said liquid sample pumping means to the first fluid passage of said fluid flow assembly for providing liquid sample in the connected condition, and providing for particle-free liquid flow in a reverse direction through the first fluid passage of said fluid flow assembly for flushing in the disconnected condition of the connecting means.

13. In a liquid sample scanning, analyzing, separating, or like apparatus as defined in claim 12 wherein said removable connecting means includes, a hand-held pick-up and delivery tube connected through conduit to said pumping means, and an injection cone connected through conduit to said first fluid passage, said pick-up and delivery tube being removably insertable into said cone in fluid-tight frictional engagement therewith during pumping of liquid samples to the scanning device.

14. In a liquid sample scanning, analyzing, separating, or like apparatus as defined in claim 13 including, means for removing particle-free liquid from said injection cone which liquid is supplied thereto when the hand-held pick-up and delivery tube is removed therefrom.

15. In a liquid sample scanning, analyzing, separating, or like apparatus as defined in claim 12 wherein said pumping means comprises a motor-operated syringe.

16. In a liquid sample scanning, analyzing, separating, or like apparatus as defined in claim 12 including visual display means for display of operator instructions involving operation of said hand-held pick-up and delivery tube.

17. In a liquid sample scanning, analyzing, separating, or like apparatus as defined in claim 16 including, supporting means for support of a multi-well tray of light-transmitting material, which wells contain liquid samples to be delivered to the scanning apparatus, said visual display means being located at said tray supporting means for viewing by the operator through a tray supported thereat.

18. In a liquid sample scanning, analyzing, separating, or like apparatus as defined in claim 17 including a stored program digital computer to which said liquid sample pumping means and visual display means are responsive for control of said pumping and visual display means, respectively.

19. In a liquid sample scanning, analyzing, separating, or like apparatus as defined in claim 18 of the type which includes sample sensing means and data acquisition means for storing data supplied thereto from said sensing means, including circuit means including interface circuit means for supplying sample source identification signal means to said visual display means and to said data acquisition means for identifying tray wells from which liquid samples are to be obtained for delivery to said scanning apparatus and for providing an association between data stored by said data acquisition means and the tray well from which the sample was obtained, respectively.

20. A method of obtaining information on characteristics of liquid samples obtained from a plurality of liquid sample sources comprising, producing a signal for identifying the liquid sample source from which a liquid sample is to be obtained, supplying said liquid sample source identifying signal to visual display means for visually indicating to the operator from which liquid sample source the next liquid sample is to be obtained, under operator control, obtaining liquid sample from the visually-indicated liquid sample source and feeding said liquid sample obtained from the identified source to sample sensing means for obtaining data related to at least one characteristic of the sample, and associating the liquid sample source identifying signal with data obtained from said sample sensing means for identifying said data with the associated liquid sample source from which the sample was obtained.

21. A method as defined in claim 20 which includes, obtaining liquid samples for feeding the said sample sensing means from wells of a multi-well light-transmitting tray.

22. A method as defined in claim 21 which includes, positioning said tray over said visual display means for viewing thereof through said tray.

23. A method as defined in claim 20 which includes, supplying said liquid sample source identifying signal and data obtained from said sample sensing means to data acquisition means in performance of said associating step.

24. A method of feeding liquid samples to a scanning device from a sample delivery system, said scanning device including a nozzle assembly comprising coaxial inner and outer nozzles to which liquid samples and sheath fluid are supplied, respectively, for producing a coaxial flow stream, sample sensing means for obtaining data related to at least one characteristic of the sample included in the flow stream, and data acquisition means to which data from said sample sensing means are supplied, said sample delivery system including a pump connected through a conduit to a hand-held pick-up and delivery tube, and releasable coupling means for fluid-tight coupling said hand-held pick-up and delivery tube to the inner nozzle of said nozzle assembly in the connected condition and for disconnection of the hand-held pick-up and delivery tube from the inner nozzle in the disconnected condition of the releasable coupling means, said method comprising, backflushing said inner nozzle by disconnecting said hand-held pick-up and delivery tube from the inner nozzle to allow reverse flow of sheath fluid therethrough, connecting said hand-held pick-up and delivery tube to said inner nozzle, and driving a liquid sample from said hand-held pick-up and delivery tube through said inner nozzle for flow through said scanning device.

25. A method of feeding as defined in claim 24 wherein wash liquid also is driven from said hand-held pick-up and delivery tube while driving the liquid sample through the scanning device, performing the following steps while said hand-held pick-up and delivery tube is disconnected from said inner nozzle, replacing wash liquid driven from said hand-held pick-up and delivery tube, drawing an air bubble into said hand-held pick-up and delivery tube for use in separating wash liquid from a liquid sample to be drawn into said hand-held pick-up and delivery tube, and withdrawing a liquid sample into said hand-held pick-up and delivery tube from a liquid sample container.

26. A method of feeding as defined in claim 25 which includes, expelling a small amount of liquid sample from said hand-held pick-up and delivery tube to clear the end thereof of air bubbles before connecting said hand-held pick-up and delivery tube to said inner nozzle.

27. A method of feeding as defined in claim 24 wherein said connecting step includes urging the end of the pick-up and delivery tube into fluid-tight engagement within an injection cone connected through a conduit to said inner nozzle.

28. In a liquid delivery system for feeding liquid samples, the combination comprising, liquid sample pumping means, and means for removably connecting said liquid sample pumping means to a fluid flow passage for providing liquid samples to a fluid flow passage in the connected condition, said removable coupling means including a pick-up and delivery tube connected through conduit to said pumping means, and an injection cone connected to the fluid flow passage, said pick-up and delivery tube being removably insertable into said cone in fluid-tight frictional engagement therewith during pumping of liquid samples to the fluid flow passage.

29. In a liquid delivery system as defined in claim 28 including, means for removing liquid from said injection cone supplied thereto from the fluid flow passage when the pick-up and delivery tube is removed from the injection cone.

30. In a liquid delivery system as defined in claim 28 wherein said pumping means comprises a motor-operated syringe.

31. In a liquid delivery system as defined in claim 28 wherein said pick-up and delivery tube is hand-held, said system including, visual display means for display of operator instructions involving operation of said hand-held pick-up and delivery tube.

32. In a liquid delivery system as defined in claim 31 including, supporting means for support of a multi-well tray of light-transmitting material, which wells are adapted to contain liquid samples to be delivered, said visual display means being located at said tray supporting means for viewing by the operator through a tray supported thereat.

33. In a liquid sample delivery system as defined in claim 32 including, a stored program digital computer to which said liquid sample pumping means and visual display means are responsive for control of said pumping and visual display means, respectively.

34. In a liquid sample delivery system as defined in claim 33 including, circuit means including interface circuit means for supplying sample source identification signal means to said visual display means and to a device to which the fluid flow passage is connected for identifying tray wells from which liquid samples are to be obtained for delivery to the device and for providing an association between data from said device and the tray well from which the sample was obtained, respectively.

35. In a liquid delivery system for feeding liquid samples, the combination comprising, liquid sample pumping means, a hand-held pick-up and delivery tube connected through conduit to said pumping means, visual display means for display of operator instructions involving operation of said hand-held pick-up and delivery tube, and supporting means for support of a multi-well tray of light-transmitting material, which wells are adapted to contain liquid samples to be delivered, said visual display means being located at said tray supporting means for viewing by the operator through a tray supported thereat.

36. In a liquid delivery system as defined in claim 35 including, a stored program digital computer to which said liquid sample pumping means and visual display means are responsive for control of said pumping and visual display means, respectively.

37. In a liquid delivery system as defined in claim 36 including, circuit means including interface circuit means for supplying sample source identification signal means to said visual display means and to a device to which liquid samples are pumped for identifying tray wells from which liquid samples are to be obtained for delivery to the device and for providing an association between data from said device and the tray well from which the sample was obtained, respectively.

38. In a liquid delivery system as defined in claim 37 wherein said device to which said sample source identification signal means is supplied includes means for recording said sample source identification signal means and associated data from said device to provide a record of said association for future reference.

* * * * *